(12) United States Patent
Lambert et al.

(10) Patent No.: US 8,158,614 B2
(45) Date of Patent: Apr. 17, 2012

(54) THERAPEUTIC TREATMENT OF CANCER AND DYSPLASIA OF THE CERVIX OR VAGINA USING ESTROGEN ANTAGONISTS

(75) Inventors: Paul F. Lambert, Madison, WI (US); SangHyuk Chung, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 26 days.

(21) Appl. No.: 12/693,850

(22) Filed: Jan. 26, 2010

(65) Prior Publication Data

US 2010/0203164 A1 Aug. 12, 2010

Related U.S. Application Data

(60) Provisional application No. 61/147,667, filed on Jan. 27, 2009, provisional application No. 61/148,445, filed on Jan. 30, 2009, provisional application No. 61/261,615, filed on Nov. 16, 2009.

(51) Int. Cl.
| | | |
|---|---|---|
| A61K 31/56 | (2006.01) | |
| A61K 31/445 | (2006.01) | |
| A01N 43/40 | (2006.01) | |
| A01N 43/02 | (2006.01) | |

(52) U.S. Cl. .................. 514/182; 514/324; 514/449
(58) Field of Classification Search .................. None
See application file for complete search history.

(56) References Cited

U.S. PATENT DOCUMENTS 6,433,000 B1  8/2002  Li et al.

FOREIGN PATENT DOCUMENTS

| WO | 2005/108338 A1 | 11/2005 |
| WO | 2009/034136 A2 | 3/2009 |

OTHER PUBLICATIONS

Althius, M. D., Moghissi, K. S., Westhoff, C. L., Scoccia, B., Lamb, E. J., Lubin, J. H., and Brinton, L. A. (2005a). Uterine cancer after use of clomiphene citrate to induce ovulation. Am J Epidemiol 161, 607-615.
2. Althuis, M. D., Scoccia, B., Lamb, E. J., Moghissi, K. S., Westhoff, C. L., Mabie, J. E., and Brinton, L. A. (2005b). Melanoma, thyroid, cervical, and colon cancer risk after use of fertility drugs. Am J Obstet Gynecol 193, 668-674.
Ariazi, E. A., Lewis-Wambi, J. S., Gill, S. D., Pyle, J. R., Ariazi, J. L., Kim, H. R., Sharma, C. G., Cordera, F., Shupp, H. A., Li, T., and Jordan, V. C. (2006). Emerging principles for the development of resistance to antihormonal therapy: implications for the clinical utility of fulvestrant. J Steroid Biochem Mol Biol 102, 128-138.
Brake, T., Connor, J. P., Petereit, D. G., and Lambert, P. F. (2003). Comparative analysis of cervical cancer in women and in a human papillomavirus-transgenic mouse model: identification of minichromosome maintenance protein 7 as an informative biomarker for human cervical cancer. Cancer Res 63, 8173-8180.

Brake T., and Lambert, P. F. (2005). Estrogen contributes to the onset, persistence, and malignant progression of cervical cancer in a human papillomavirus-transgenic mouse model. Proc Natl Acad Sci U S A 102, 2490-2495.
Buchanan D. L., Kurita, T., Taylor, J. A., Lubahn, D. B., Cunha, G. R., and Cooke, P. S. (1998). Role of stromal and epithelial estrogen receptors in vaginal epithelial proliferation, stratification, and cornification. Endocrinology 139, 4345-4352.
Cavalieri E., Chakravarti, D., Guttenplan, J., Hart, E., Ingle, J., Jankowiak, R., Muti, P., Rogan, E., Russo, J., Santen, R., and Sutter, T. (2006). Catechol estrogen quinones as initiators of breast and other human cancers: implications for biomarkers of susceptibility and cancer prevention. Biochim Biophys Acta 1766, 63-78.
Chung SH, Wiedmeyer K, Shai A, Korach KS, and Lambert PF, 2008. Requirement for estrogen receptor alpha in a mouse model for human papillomavirus-associated cervical cancer. Cancer Res. 68: 9928-9934.
Chung SH and Lambert PF. 2009. Prevention and treatment of cervical cancer in mice using estrogen receptor antagonists. Proc. Natl. Acad. Sci. U. S. A. 106:19467-19472.
Elson D. A., Riley, R. R., Lacey, A., Thordarson, G., Talamantes, F. J., and Arbeit, J. M. (2000). Sensitivity of the cervical transformation zone to estrogen-induced squamous carcinogenesis. Cancer Res 60, 1267-1275.
Friedrich M., Mink, D., Villena-Heinsen, C., Woll-Hermann, A., and Schmidt, W. (1998). Tamoxifen and proliferation of vaginal and cervical epithelium in postmenopausal women with breast cancer. Eur J Obstet Gynecol Reprod Biol 80, 221-225.
Heldring, N., Pike, A., Andersson, S., Matthews, J., Cheng, G., Hartman, J., Tujague, M., Strom, A., Treuter, E., Warner, M., and Gustafsson, J. A. (2007). Estrogen receptors: how do they signal and what are their targets. Physiol Rev 87, 905-931.
Moreno, V., Bosch, F. X., Munoz, N., Meijer, C. J., Shah, K. V., Walboomers, J. M., Herrero, R., and Franceschi, S. (2002). Effect of oral contraceptives on risk of cervical cancer in women with human papillomavirus infection: the IARC multicentric case-control study. Lancet 359, 1085-1092.
Munoz, N., Franceschi, S., Bosetti, C., Moreno, V., Herrero, R., Smith, J. S., Shah, K. V., Meijer, C. J., and Bosch, F. X. (2002). Role of parity and human papillomavirus in cervical cancer: the IARC multicentric case-control study. Lancet 359, 1093-1101. Nair, H. B., Luthra, R., Kirma, N., Liu, Y. G., Flowers, L., Evans, D., and Tekmal, R. R. (2005). Induction of aromatase expression in cervical carcinomas: effects of endogenous estrogen on cervical cancer cell proliferation. Cancer Res 65, 11164-11173.
Palmieri C., Cheng, G. J., Saji, S., Zelada-Hedman, M., Warri, A., Weihua, Z., Van Noorden, S., Wahlstrom, T., Coombes, R. C., Warner, M., and Gustafsson, J. A. (2003). Estrogen receptor beta in breast cancer. Endocr Relat Cancer 9, 1-13.
Riley R. R., Duensing, S., Brake, T., Munger, K., Lambert, P. F., and Arbeit, J. M. (2003). Dissection of human papillomavirus E6 and E7 function in transgenic mouse models of cervical carcinogenesis. Cancer Res 63, 4862-4871.
Rossing, M. A., Daling, J. R., Weiss, N. S., Moore, D. E., and Self, S. G. (1996). In situ and invasive cervical carcinoma in a cohort of infertile women. Fertil Steril 65, 19-22.

(Continued)

Primary Examiner — Brandon Fetterolf
Assistant Examiner — Anna Pagonakis
(74) Attorney, Agent, or Firm — Quarles & Brady LLP (57) ABSTRACT

A method for treatment of cervical or vaginal cancer and their associated dysplasia, including the steps of identifying a human cervical or vaginal cancer and/or dysplasia patient, administering an effective amount of an estrogen antagonist therapy to the patient, wherein the amount is effective to reduce cancer and dysplasia symptoms, and observing a reduction of cancer and dysplasia symptoms in the patient.

3 Claims, 3 Drawing Sheets

OTHER PUBLICATIONS

Shai, A., Brake, T., Somoza, C., and Lambert, P. F. (2007). The human papillomavirus E6 oncogene dysregulates the cell cycle and contributes to cervical carcinogenesis through two independent activities. Cancer Res 67, 1625-1635.

Shelly, W., Draper, M. W., Krishnan, V., Wong, M., and Jaffe, R. B. (2008). Selective estrogen receptor modulators: an update on recent clinical findings. Obstet Gynecol Surv 63, 163-181.

Robertson JF, Fulvestrant (Faslodex)—How to Make a Good Drug Better, Oncologist 2007 12:774-84.

Cline J, Neoplasms of the Reproductive Tract: The Role of Hormone Exposure, ILAR, 2004; 45(2):179-88.

Jordan VC. Chemoprevention of breast cancer with selective estrogen receptor modulators. Nat Rev Cancer Jan. 2007;7(1):46-53.

Aggarwal et al. Molecular Targets and Anticancer Potential of Indole-3-Carbinol and Its Derivatives, Cell Cycle, Sep. 2005, 4(9):1201-15.

Jin et al., Indole-3-Carbinol Prevents Cervical Cancer in Human Papilloma Virus Type 16 (HPV16) Transgenic Mice, Cancer Res., Aug. 1999, 15:59(16):3991-7.

Bell et al., Placebo-Controlled Trial of Indole-3-Carbinol in the Treatment of CIN, Gynecol Oncol., Aug. 2000, 78(2):123-9.

Arbeit et al., Chronic estrogen-induced cervical and vaginal squamous carcinogenesis in human papillomavirus type 16 transgenic mice, PNAS USA, 1996 93(7):2930-35.

Vargas Roig et al., Effects of Short-Term Tamoxifen Administration in Patients with Invasive Cervical Carcinoma, Anticancer Research 13: 2457-2464 (1993).

Kelley et al., Modulation of the Folate Receptor or Gene by the Estrogen Receptor: Mechanism and Implications in Tumor Targeting, Cancer Research 63, 2820-2828, Jun. 1, 2003.

Carthew et al., Tamoxifen induces endometrial and vaginal cancer in rats in the absence of endometrial hyperplasia, Carcinogenesis vol. 21 No. 4 pp. 793-797, 2000.

Carcinogeneis 5: Hormones and Cancer, Proceedings of the American Association for Cancer Research, vol. 40, Mar. 1999.

Dasari et al., A Rare Case of Liver Metastasis in Malignant Melanoma of the Vagina, Journal of Gynecologic Surgery, vol. 25, No. 1, 2009.

Ma et al., Malignant mixed mullerian tumor of primary mesenteric origin associated with a synchronous ovarian cancer: case report and literature review, Eur. J. Gynaecol. Onco. 2008, 29(3), 289-93.

Chung et al., Prevention and treatment of cervical cancer in mice using estrogen receptor antagonists, PNAS, Nov. 17, 2009, vol. 106., No. 46, 19467-19472.

PCT Search Report and Written Opinion of US/PCT/2010/022069 mailed Apr. 5, 2010.

THERAPEUTIC TREATMENT OF CANCER AND DYSPLASIA OF THE CERVIX OR VAGINA USING ESTROGEN ANTAGONISTS

CROSS REFERENCE TO RELATED APPLICATIONS

This application claims the benefit of U.S. Provisional Application Ser. No. 61/147,667, filed Jan. 27, 2009, U.S. Provisional Application Ser. No. 61/148,445, filed Jan. 30, 2009, and U.S. Provisional Application Ser. No. 61/261,615, filed Nov. 16, 2009. Each of these applications is incorporated by reference.

STATEMENT REGARDING FEDERALLY SPONSORED RESEARCH OR DEVELOPMENT

This invention was made with United States government support awarded by the following agency:
NIH CA120847
The United States government has certain rights in this invention.

BACKGROUND OF THE INVENTION

High-risk human papillomavirus (HPV) types, particularly HPV16, are causally associated with human malignancies including cervical and vaginal cancers in women (zur Hausen H, 2002). New prophylactic HPV vaccines can prevent infections by a subset of these HPVs; however, they will not eliminate pre-existing HPV infections, new infections by high-risk HPVs not targeted by the vaccines, or cervical cancers and precancerous lesions that arise from those HPV infections (Roden and Wu, 2006). Traditional therapeutic approaches (for example, surgery, radiotherapy, and chemotherapy) are of limited value to patients with advanced or recurrent cervical cancer. Consequently, cervical cancer remains the second leading cause of death by cancer among women worldwide (zur Hausen H, 2002; Roden and Wu, 2006). New, more effective therapeutic strategies are clearly needed. Herein, a potent new therapeutic approach that not only effectively treats preexisting cervical and vaginal cancers but also can prevent their onset is identified.

The uterine cervix is highly responsive to steroidal hormones such as estrogen. Correspondingly, cervical cancers most commonly arise in the 3rd-5th decades, which typically correspond to the pre-menopausal period of life in women (Cline, 2004). Furthermore, use of oral contraceptives or high parity has been shown to significantly increase the risk for cervical cancer in HPV-infected women (Moreno et al., 2002; Munoz N et al., 2002). These observations raise the possibility that steroidal hormones such as estrogen might affect cancers of the cervix, much like that of other hormonally responsive female organs (Cline, 2004; Jordan, 2007). Estrogen replacement therapy alone, however, does not increase the risk for cervical cancer, and tamoxifen, a well-known estrogen receptor antagonist in the breast, has no beneficial effect on cervical cancer (Bigler et al., 2004; Persson et al., 1996). Unfortunately, neither of these studies controlled for infections with high-risk HPVs that are prerequisite for cervical cancer (zur Hausen H, 2002; Roden and Wu, 2006). Furthermore, tamoxifen has an estrogen receptor (ER) agonistic rather than antagonistic effect in the human cervix (Friedrich et al., 1998). Studies have shown a protective effect on cervical cancer by indole-3-carbinol, a compound found in cruciferous vegetables that favorably alters the metabolism of estrogen; however, this drug has also been shown to inhibit the genesis of other tumors that are not believed to depend upon estrogen (Aggarwal and Ichikawa, 2005; Jin et al., 1999; Bell et al., 2000). Thus, the evidence for or against a role of estrogen in cervical carcinogenesis in humans has been limited in nature and inconclusive.

To elucidate mechanisms by which HPV oncogenes promote cervical cancer and by which cofactors contribute to cervical carcinogenesis, we have generated transgenic mouse models that express HPV16 E6 and/or E7 under the control of human keratin 14 promoter that drives gene expression in stratified squamous epithelia, natural targets for HPV infection. The progressive disease that arises in these mouse models recapitulates various aspects of human cervical disease, including the multiple stages of cervical carcinogenesis, the anatomical location and histopathological nature of the cancers, and the expression patterns of various biomarkers (Brake et al., 2003; Elson et al., 2000), validating the relevance of these preclinical models to cervical disease in women. Using these mouse models, we have demonstrated that estrogen is required for development of cervical cancer and that estrogen receptor alpha (ERα) is crucial for the development of atypical squamous metaplasia (ASM), which has been proposed to be the very first step of cervical carcinogenesis preceding the development of cervical intraepithelial neoplasia (CIN), a precancerous cervical lesion that can progress to cervical cancer (Elson et al., 2000; Brake and Lambert, 2005; Chung et al., 2008; Shai et al., 2007; Arbeit et al., 1996; Riley RR, et al. 2003). It is still unclear, however, whether ER-α is crucial for the progression of CIN lesions to invasive cancer and maintenance of cervical cancer. Herein, it is demonstrated that inhibition of ER is effective in both treating and preventing cervical cancer in mice.

SUMMARY OF THE INVENTION

In one aspect according to the present invention, a method for treatment of cervical or vaginal cancer or their associated dysplasia (CINI-III, VINI-III)) is disclosed. The method includes the steps of identifying a human cervical or vaginal cancer and/or dysplasia (CIN/VIN) patient and administering an effective amount of an estrogen antagonist therapy to the patient. The amount is effective to reduce cancer and dysplasia symptoms. The method further includes observing a reduction of cancer and dysplasia symptoms in the patient.

In a second aspect according to the present invention, a method for preventing cervical or vaginal cancer in patients with dysplasia is disclosed. The method includes the steps identifying a dysplasia (CIN/VIN) patient and administering an effective amount of an estrogen antagonist therapy to the patient. The amount is effective to reduce dysplasia symptoms and prevent cervical cancer. The method further includes measuring a reduction of dysplasia symptoms and absence or slowing of progression to cervical/vaginal cancer.

In a third aspect according to the present invention, a method for preventing recurrence of cervical or vaginal cancers is disclosed. The method includes the steps of identifying a human cervical or vaginal cancer patient who has been successfully treated to remove detectable cancer, administering an effective amount of an estrogen antagonist therapy to the patient, and monitoring for persistence of a disease-free state.

In a fourth aspect according to the present invention, a method of treating ERα-dependent spreading or metastatic cancers of cervical or vaginal tissue origin is disclosed. The method includes identifying a human cancer patient with spreading or metastatic cancer of cervical or vaginal tissue origin, administering an effective amount of an estrogen antagonist therapy to the patient, and measuring reduction of cancer symptoms in the patient.

DESCRIPTION OF THE DRAWINGS

FIG. 1A shows low magnification images of representative H&E-stained endocervical sections from each group of mice described in Tables 1 and 2. FIG. 1B shows high magnification images of representative H&E-stained lower reproductive tracts. In both FIGS. 1A and 1B CIN2/3 lesions as well as cancers are evident in mice not treated with fulvestrant (left two panels) but are absent in mice treated with fulvestrant (right two panels). Note also that dysplasia is absent in mice treated for only 2 weeks with fulvestrant but cancers remain.

FIG. 2. Cancers remaining after one-month fulvestrant treatment are associated with non-hypoplastic epithelium. Shown in the left panels are low magnification images of the two cancers (one cervical—upper panel, the other vaginal—lower panel) that persisted in 2 of 13 mice treated with fulvestrant for one month. In the right panels are high magnification images of cervical (upper panel) or vaginal (lower panel) epithelium that was immediately juxtaposed to these two cancers. Note the non-hypoplastic (i.e., thick) epithelium akin to what is seen in female mice in normal estrus. This is in stark contrast to the hypoplastic epithelia found elsewhere in the reproductive tracts of these same fulvestrant-treated mice (see inset images in right panels), as well as in the other fulvestrant treated mice (see FIG. 1B).

FIG. 5. Effectiveness of fulvestrant in blocking growth in ERα-positive vs. ERα-negative cervical cancer cell lines. Estrogen-treated nude mice were injected with CVX1 (a) or CaSki (b) cells. Once tumors formed, one group of mice was treated with fulvestrant twice a week and the other group was left untreated. Tumor growth was monitored every week (a) or every 4 days (b). Tumor size was determined by the diameter of cross sectional area and starting size was set at 100%. CVX1 tumor size at the time of fulvestrant treatment was 7.7±2.4 mm and that of the untreated group was 3.9±1.5 mm. CaSki tumor size in both groups was 3 mm on average.

DESCRIPTION OF THE INVENTION

A. Introduction

Despite the recent advent of human papillomavirus (HPV) vaccines, HPV-associated cancers of the lower female reproductive tract, cervical cancer being most common among these, remain a great health burden worldwide and are predicted to remain so for at least the next three decades. Cervical cancer alone is the second most common cancer in women and the second most frequent cause of death by cancer in women worldwide (Sankaranarayanan and Ferlay, 2006). Current therapeutic approaches for treating patients with cervical cancer, primarily radio- and chemo-therapies, have limited success, with 5-year survival rates being less than 50% worldwide (Sankaranarayanan and Ferlay, 2006).

Cervical cancers arise through multiple steps, cervical intraepithelial neoplasia 1 (CIN1, low-grade dysplasia), CIN2 (mid-grade dysplasia), CIN3 (high-grade dysplasia), and then finally invasive cancer. Although CIN lesions may regress spontaneously, CIN3 is normally treated due to its high rate of progression to cancer. Treatment of cervical dysplasias traditionally involves surgical procedures such as Loop Electrosurgical Excision Procedure (LEEP) and cryo/laser therapies, all of which are associated with complications (Hunter et al., 2008a; Hunter et al., 2008b).

Virtually all cervical cancers are associated with the so-called high-risk human papillomaviruses (HPVs), among which HPV-16 is most common, being found in approximately 60% of all cervical cancers (Burd, 2003). A newly available vaccine that inhibits infection by a subset of cancer-causing HPVs including HPV-16 shows promise for reducing cervical cancer in future generations of women who make use of this vaccine (FUTURE II Group, 2007; Villa, 2007). It is clear, however, that more effective strategies are warranted for current generations of women who are already exposed to high-risk HPVs and for future generations of women who are not vaccinated or become infected with cancer-causing HPVs not targeted by currently available vaccines. Furthermore, a specific non-invasive therapy for cervical cancer and/or dysplasia is currently unavailable, as described above.

Although it is well established that HPV is the major etiological factor for cervical carcinogenesis, HPV infection alone is not sufficient for the development of cervical cancer because only a minor fraction of patients infected with HPV develop cervical cancer and CIN lesions often regress without treatment (Schiffman et al., 2007). Several cofactors including long-term use of oral contraceptives and high parity have been implicated in the genesis of HPV-associated cervical cancer (Moreno et al., 2002; Munoz et al., 2002). These results raise a possibility that, in addition to HPV, female steroid hormones such as estrogen may play a crucial role in cervical carcinogenesis similar to breast cancers (Palmieri et al., 2002).

It is relevant that infertile women using an anti-estrogen, clomiphene citrate, have reduced cervical cancer incidence compared to non-users (Rossing et al., 1996). This study, however, did not control for HPV infection that is prerequisite for the development of cervical cancer (Woodman et al., 2007; zur Hausen, 2002). In addition, it is difficult to reconcile conflicting observations that use of clomiphene citrate increases risk for uterine and breast cancers (Althuis et al., 2005a; Lerner-Geva et al., 2006). Furthermore, another study showed that infertile women using clomiphene citrate have slightly higher risk for cervical cancer, though statistically not significant (Althuis et al., 2005b).

Other studies argue that cervical cancers do not rely upon estrogen, but those studies also have caveats. For instance, one observational study without controlling for HPV infection argues that hormone replacement therapy with estrogen alone or estrogen-progestin combination does not increase risk of cervical cancer (Persson et al., 1996). Another clinical study demonstrates that a selective estrogen receptor modulator (SERM) tamoxifen has no beneficial effect on cervical cancer, leading to the conclusion that cervical cancer is estrogen-independent (Bigler et al., 2004). An assumption of this study was that tamoxifen is an antagonist for estrogen receptor (ER) in the cervix as in the breast. It has been shown, however, that tamoxifen has an agonistic rather than antagonistic effect on ER function in the human cervix (Friedrich et al., 1998). Furthermore, it is difficult to interpret the relevance of confounding responses of different cervical cancer cell lines to estrogen and various SERMs because these cells have been adapted to growth in tissue culture for decades, and therefore, may not be adequately representational of in vivo conditions, and expression patterns of ER are poorly characterized (Herynk and Fuqua, 2004). Thus, there remains a poor understanding of the estrogen-dependence of cervical cancers in humans.

An essential role of estrogen in cervical cancer has been clearly defined in mouse models for HPV-associated cervical cancer that make use of transgenic mice expressing major HPV oncogenes E6 or E7, or both under the control of human keratin 14 (K14) promoter, which drives transgene expression in stratified squamous epithelia, natural HPV infection sites. In these mouse models, either an HPV oncogene or estrogen alone is insufficient to cause cervical cancers, whereas an HPV oncogene in conjunction with physiological levels of exogenous estrogen can promote the development of cervical cancer (Brake and Lambert, 2005; Elson et al., 2000; Riley et al., 2003; Shai et al., 2007). The progressive cervical disease that arises in these mouse models recapitulates various aspects of human cervical disease, including the multiple stages of cervical carcinogenesis (atypical squamous metaplasia, CIN 1-3, and then cancer), anatomical location (cancers primarily arising from the transformation zone), histopathological nature of the cancers, and the expression patterns of various biomarkers (Brake et al., 2003; Elson et al., 2000).

It is hypothesized that estrogen can contribute to the development of cancers by ER-dependent and -independent mechanisms. Estrogen is best known for exerting its physiological effects by binding and activating its receptors, ERα and/or ERβ (Couse and Korach, 1999). The mitogenic effects of estrogen that are mediated through ERα are crucial for the development and maintenance of most human breast cancers (Palmieri et al., 2002). ERα-positive breast cancers are highly responsive to the therapy with SERMs such as tamoxifen and fulvestrant that directly bind and inhibit the function for ERα (Heldring et al., 2007). The function for ERβ in breast cancer and other estrogen-dependent cancers is less well understood. The potential ER-independent mechanism involves estrogen metabolites that can function as a direct carcinogen inducing detrimental genetic mutations (Cavalieri et al., 2006). However, it remains unclear to what extent this mechanism contributes to estrogen's role in estrogen-dependent cancers.

With regard to the mechanism by which estrogen cooperates with HPV oncogenes in murine cervical carcinogenesis, we have recently obtained evidence that estrogen functions through ERα, as ERα null mice expressing E7 (K14E7/ERα$^{-/-}$) lack cervical cancers as well as CIN even after treatment with estrogen for 6 months. It is still unclear, however, whether ERα is crucial for the progression to and maintenance of cervical cancer and CIN lesions because K14E7/ERα$^{-/-}$ mice treated with estrogen fail to develop atypical squamous metaplasia that has been proposed to be the very first step of cervical carcinogenesis preceding the development of CIN (Chung et al., 2008).

In the Examples presented below, we examined whether anti-estrogens have a beneficial effect on treating and preventing cervical cancers arising in K14E6/K14E7 double transgenic mice treated with estrogen for 6 months, as well as on treating tumor formation in a human cervical cancer model promotes regression and prevention of cervical and vaginal disease including cancer. Our second example demonstrates that raloxifene, a selective estrogen receptor modulator (SERM), also promotes regression of cervical and vaginal disease including cancer. Our third example demonstrates that fulvestrant prevents the development of cervical cancer. The fourth example demonstrates that estrogen facilitates tumor formation by an ERα-positive human cervical cancer cell line (CVX1) in nude mice and that fulvestrant inhibits tumor growth by this cell line.

B. Method of Treating and Preventing Cervical and Vaginal Cancers

In one embodiment, the present invention is a method of treating cervical or vaginal cancer and dysplasia comprising the administration of an anti-estrogen to a cervical or vaginal cancer and/or cervical or vaginal dysplasia patient. In a preferred embodiment, one would (1) obtain a diagnosis of cancer or dysplasia in a patient, (2) administer an effective amount of an estrogen antagonist, wherein the amount is effective to reduce cancer or dysplasia symptoms, and (3) examine the patient for reduction of cancer symptoms. Section (C) below discloses preferred anti-estrogen therapies.

One would obtain a diagnosis of cervical/vaginal cancer or dysplasia through conventional means. For example, one may refer to Jhingran et al., Churchill Livingstone Elsevier Press, Philadelphia (2008), pp 1745-1792.

The paragraphs below describe a preferred prophetic treatment of a human cervical cancer and dysplasia patient:

We have found that estrogen antagonist therapies, such as fulvestrant and raloxifene, have multiple applications in the treatment of squamous cell carcinoma of the uterine cervix or vagina. These applications could be applied in both pre-menopausal and post-menopausal women. Estrogen antagonist therapy could be considered as primary single agent therapy or be used in combination with other classic chemotherapy agents, such as platinum and taxane molecules, as anti-estrogen therapy may enhance the cytotoxic effects of these drugs (despite the fact that squamous cell carcinomas are historically felt to be largely resistant to such medications). Clearly the most straightforward application would be as therapy in pre-menopausal and peri-menopausal women wherein estrogen, arising systemically or from the lesion itself, is a driving factor in tumor development, maintenance and/or progression.

In general, eligible patients for this type of treatment would have a diagnosis of cervical/vaginal cancer with a documented occurrence or recurrence of disease that is measurable by clinical exam or radiologic studies (such as CT scans). Once identified as subjects, women will be treated with estrogen antagonist therapy per established dosing regimens (derived primarily from breast cancer treatment). If fulvestrant is the selected anti-estrogen, preferable treatment would include loading doses of 500 milligrams on day 1 and 14 and then monthly dosing at one of two standard doses, 250 mg or 500 mg every 28 days (Robertson J F., Oncologist. 2007 12:774-84) delivered IM. One may wish to optimize the dosage for cervical cancer. Doses of between 50-1000 mg would be considered useful. Treatment with the anti-estrogen could be done alone or in conjunction with existing chemotherapeutic modalities.

Preferably, patients will be seen every 28 days and tumor measurements for response checked every other month. Responses will be defined by standard RECIST (Therasse P, et al. J Nat Cancer Inst 2000; 92:205-16) criteria and response rates compared to those of other drugs used to treat this disease in the past. Potentially favorable response rates would be an indication to continue with optimal development in this disease. Due to the diverse hormonal status of eligible women, a treatment such as this will need to be evaluated based on such hormonal factors as menopausal status, body mass (obesity), as well as receptor status within the tumor itself and/or associated stroma. Each of these factors could influence the optimum choice and dose of anti-estrogen and the predicted responsiveness to the treatment.

As described above, in one embodiment, one would treat the patient of the present invention with fulvestrant in a manner similar to treatment of breast cancers with fulvestrant. If one elected to use other anti-estrogen therapies, e.g., raloxifene, a dose similar to that in approved use would be preferred. For example, if one wished to use raloxifene, an oral dose of between 6 and 600 mg (±10%) a day, preferably 60 mg a day, would be preferred.

In another embodiment, patients who had been treated for cervical/vaginal cancer and/or precancerous lesions would be placed on anti-estrogen therapy to prevent recurrence of disease. Such patients would be dosed as described above akin to the treatment of breast cancer patients for whom anti-estrogen therapy has proven effective at prolonging disease free state and survival.

In another embodiment, the present disclosure provides a method of treating ERα-dependent spreading or metastatic cancers of cervical or vaginal tissue origin. The method includes: (1) identifying a human cancer patient with metastatic or spreading cancer of cervical or vaginal tissue origin; (2) administering an effective amount of an estrogen antagonist therapy; and (3) observing reduction of cancer symptoms in the patient. Observation may take the form of measuring the reduction of cancer symptoms in the patient.

While not wishing to be bound by theory, it is believed that cancers of cervical and/or vaginal tissue origin prior to becoming and/or at the same time as they become metastatic, may spread from the cervix and/or vagina into immediately surrounding tissues, including for example, those associated with the peritoneum. As well, it is possible that at some point during the progression of cervical and/or vaginal cancers, metastasis will occur resulting in the spread of cervical and/or vaginal cancer cells throughout the body. To the extent that these spreading and/or metastasizing cervical and vaginal cancers are ERα-dependent, an estrogen antagonist therapy may effectively treat a resultant tumor, for example, by stopping the growth of, shrinking in size, and/or eradicating the resultant tumor. Means for measuring the efficacy of such treatment on spreading and metastatic cancers are disclosed herein elsewhere.

By improvement of cervical/vaginal cancer and dysplasia symptoms, we mean reduction in the size or complete resolution of precancerous and/or cancerous lesions including primary cancers as well as metastatic disease, absence of progression of precancerous lesions (see also part D below), absence of recurrence, and/or increased time of survival.

C. Estrogen Antagonist Therapy

The present invention is suitable for estrogen antagonist therapy. By "estrogen antagonist," we mean a composition that will act as an inhibitor of Estrogen Receptor alpha (ERα).

In one embodiment, a complete estrogen antagonist such as fulvestrant is used. By "complete estrogen antagonists," we mean estrogen receptor antagonists that act as an inhibitor to ERα and have no agonist effects in any tissue.

In other embodiments, the antagonist may be selected from the list below. (One may wish to consult Shelly, et al., CME Review article, Vol. 63, No. 3, Obstetrical and Gynecological Survey, 2008, incorporated by reference herein for lists of estrogen antagonists). These include SERMs (Selective Estrogen Receptor Modulators) that have both agonist and antagonist effects, depending on the tissue of interest. Preferable SERMs would include those that have antagonistic effects in the cervix/vagina.

| | Drug | Status | Effect in cervix, vagina and endometrium* |
|---|---|---|---|
| DRUGS TARGETING ESTROGEN-ER PATHWAY | | | |
| SERMs | Fulvestrant | approved | antagonist in cervix, vagina, and endometrium |
| | Ormeloxifene | approved | antagonist in endometrium |
| | Raloxifene | approved | neutral in endometrium |
| | Tamoxifen | approved | agonist in cervix, vagina, and endometrium |
| | Toremifene | approved | agonist in endometrium |
| | Arzoxifene | in clinical trials | antagonist in endometrium |
| | Bazedoxifene | approved in Europe only | antagonist in endometrium |
| | Pipendoxifene | in clinical trials | antagonist in endometrium |
| | Lasofoxifene | approved in Europe only | neutral in endometrium |
| | HMR-3339 | in clinical trials | undefined |
| | Ospemifene | in clinical trials | agonist in vagina and endometrium |
| | Acolbifene (EM-652) | in clinical trials | antagonist in endometrium |
| | EM-800 | clinical development terminated | antagonist in endometrium |
| | Droloxifene | clinical development terminated | agonist in endometrium |
| | Idoxifene | clinical development terminated | agonist in endometrium |
| | Levormeloxifene | clinical development terminated | agonist in endometrium |

*Undefined if not mentioned. Also note that the effect of most drugs on cervix is not defined.

D. Prevention of Cervical/Vaginal Cancers

The present invention is also useful for the prevention of cervical/vaginal cancers. This is especially appropriate in situations where a patient has been diagnosed with pre-cancerous lesions or has been treated to remove cancers but is at risk of recurrence. Treatment via the estrogen antagonist therapies of the present invention may obviate the need for surgical intervention.

We envision that use of estrogen antagonist therapies of the present invention to prevent initial or recurrent cervical/vaginal cancers will be similar to the treatment protocols. Once an appropriate patient has been identified, the patient will be treated with an effective amount of the anti-estrogen therapy such that there is no progression of the disease to cervical cancer. In another embodiment, the patient is treated and there is a slowing of the progression of the disease.

EXAMPLES

Example 1

Treatment of Cervical/Vaginal Cancers and Precancerous Cervical/Vaginal Lesions The majority of human cervical cancers are associated with the high-risk human papillomaviruses (HPVs), which encode the potent E6 and E7 oncogenes. Using a mouse model for HPV-associated cancers in the lower female reproductive tract, we have previously demonstrated that estrogen is required for genesis of cervical and vaginal cancers. These data are consistent with the observation that long-term use of oral contraceptives or multiple pregnancies significantly increases the risk for cervical cancer in HPV-infected women. Although ERα is required for the development of atypical squamous metaplasias, which is proposed to be the first step of cervical carcinogenesis preceding the development of CIN, it is unclear whether ERα is crucial for the development and maintenance of cervical/vaginal cancers.

In the present study, we examined whether an estrogen antagonist is effective in treating cervical/vaginal cancer and dysplasia arising in K14E6/K14E7 double transgenic mice treated with exogenous estrogen for 6 months. We experimentally demonstrated for the first time that a complete anti-estrogen, fulvestrant, efficiently clears cancers in the lower reproductive tracts of female mice. Also important is that fulvestrant treatment caused the complete regression of dysplastic lesions. Based on these findings, we propose the use of anti-estrogens in controlling gynecological disease in the lower reproductive tracts in women.

Materials and Methods

Mice. K14E7 and K14E6 transgenic mice were described previously (Herber et al., 1996; Song et al., 1999). Experimental mice were generated by crossing K14E7 hemizygote and K14E6 homozygote mice. Female progenies were genotyped by PCR and a slow-releasing 17β-estradiol ($E_2$) tablet (0.05 mg/60 days) (Innovative Research of America) was inserted subcutaneously under the dorsal skin every two months beginning at 4-6 weeks of age. After 6-month treatment with $E_2$, one group of mice was sacrificed immediately to evaluate cancer phenotypes (6M $E_2$ group), another group was maintained for another month without further treatment (6M $E_2$+1M without fulvestrant group), and the third group was treated with fulvestrant for a month (6M $E_2$+1M with fulvestrant group). Mice were injected intraperitoneally with 0.3 ml of bromo-deoxyuridine (BrdU) (12.5 mg/ml) 1 hr prior to euthanasia to measure cellular proliferation. Female reproductive tracts were harvested and processed as previously described (Riley et al., 2003). Mice were housed in McArdle Laboratory Animal Care Unit of the University of Wisconsin Medical School approved by the Association for Assessment of Laboratory Animal Care. All procedures were carried out according to an animal protocol approved by the University of Wisconsin Medical School Institutional Animal Care and Use Committee.

Fulvestrant treatment. Faslodex (50 mg/ml, human formulation of intramuscular injection of fulvestrant) was purchased from Astra Zeneca. Mice were subcutaneously injected with 0.15 ml (equivalent to 7.5 mg of fulvestrant) of Faslodex twice a week for a month (total of 9 injections).

Hematoxylin and eosin staining. Hematoxylin and eosin (H&E) staining was performed as previously described (Riley et al., 2003).

Statistical analyses were performed using one of a Log rank test, a two-sided Fisher's exact test, or a Wilcoxon rank sum test.

Results & Discussions

Cervical cancer incidence in K14E6/K14E7 double transgenic mice treated with estrogen for 6 months and then with fulvestrant for another month. To evaluate potential use of SERMs as therapeutics for cervical cancer, we have chosen to use fulvestrant, a complete anti-estrogen approved for clinical uses, because fulvestrant is well known to inhibit ERα in all examined mouse and human tissues, unlike tamoxifen and toremifene (Shelly et al., 2008). We first tested two doses of fulvestrant (10 mg/week and 15 mg/week) to determine an effective dose that reduces uterine wet weight after treatment for a week. The indicated dose was given to nontransgenic female mice by two injections at day 0 and day 3, and uteri were harvested and weighed at day 7. Uterine wet weight was normalized to body weight.

The dose range used was based upon the prior literature (Ariazi et al., 2006). Although 10 mg decreased uterine wet weight by 50%, 15 mg caused further reduction in uterine wet weight by 70% (data not shown). We chose 15 mg/week of fulvestrant to ensure maximum effect of fulvestrant on female reproductive tracts. We also used K14E6/K14E7 double transgenic mice to ensure high incidence of cervical cancer and more closely mimic clinical settings in which both E6 and E7 genes are always present (Brake and Lambert, 2005; zur Hausen, 2002). Mice were treated with exogenous $E_2$ (using slow release pellets that deliver 0.05 mg/60 days, a physiological dose sufficient to induce continuous estrus) for 6 months, a treatment period sufficient for the development of cervical cancers in 95% of K14E6/K14E7 double transgenic mice (Riley et al., 2003). Mice were subsequently injected with fulvestrant as described in Materials and Methods. Reproductive tracts were harvested, fixed in para-formaldehyde (PFA), and embedded in paraffin. Every tenth 5 μM section was stained with H&E and histopathologically scored to identify the worst grade of cervical/vaginal disease present in each animal. Consistent with previous results (Riley et al., 2003), all of K14E6/K14E7 mice treated for six months with estrogen (6M $E_2$ group) developed cancers in the lower reproductive tracts (cervix and vagina) (Tables 1 and 2). All mice that were treated with estrogen for 6 months and maintained for another month without further treatment (6M $E_2$+1M without fulvestrant group) also developed lower reproductive tract cancers at a level similar to those of the 6M $E_2$ group (Tables 1 and 2). Strikingly, mice that were treated with estrogen for 6 months and then subsequently treated with fulvestrant for one month (6M $E_2$+1M with fulvestrant group) displayed dramatically reduced cancer incidence (15%) (p=0.0001, compared to 6M $E_2$+1M without fulvestrant group, two-sided Fisher's exact test).

Comparison of cancers in K14E6/K14E7 double transgenic mice in three different treatment groups. To determine whether withdrawal of exogenous estrogen for a month results in partial regression of cervical cancer, we compared cancers arising in 6M $E_2$ group and 6M $E_2$+1M without fulvestrant group (Table 2). These two groups showed comparable cancer incidence, average size of the largest tumors (p>0.5), and cancer multiplicity (p=0.09). However, treatment with fulvestrant for one month caused highly significant reduction in all three cancer-characteristics compared to both 6M $E_2$ and 6M $E_2$+1M without fulvestrant groups (p<0.003, two-sided Fisher's exact test or Wilcoxon rank sum test) (Table 2). We have previously shown that withdrawal of exogenous estrogen for three months results only in partial regression of cervical cancers, which is much less dramatic than fulvestrant treatment (p=0.009, two-sided Fisher's exact test). Taken together, we conclude that endogenous estrogen plays a role in maintaining cervical cancer in K14E6/K14E7 double transgenic mice.

Comparison of vaginal disease in K14E6/K14E7 double transgenic mice in three different treatment groups. Because too small a number of vaginal cancers arose in our experimental animals, it was difficult to compare three groups of mice described above for cancer characteristics such as cancer incidence, tumor multiplicity, and cancer size. Instead, we compared overall vaginal disease states in those mice by giving arbitrary scores for each disease state as described in Table 1. It was notable that the treatment with fulvestrant led to highly significant reduction in severity of vaginal disease compared to that in non-treated mice (p=0.0008, two-sided Wilcoxon rank sum test) (Table 1), whereas the 6M E2 group and the 6M E2+1M without fulvestrant group displayed a similar degree of vaginal disease (p=0.6). It was also noted that cervical disease is more severe than vaginal disease (p=0.0004, two-sided Wilcoxon rank sum test).

Figure 1:
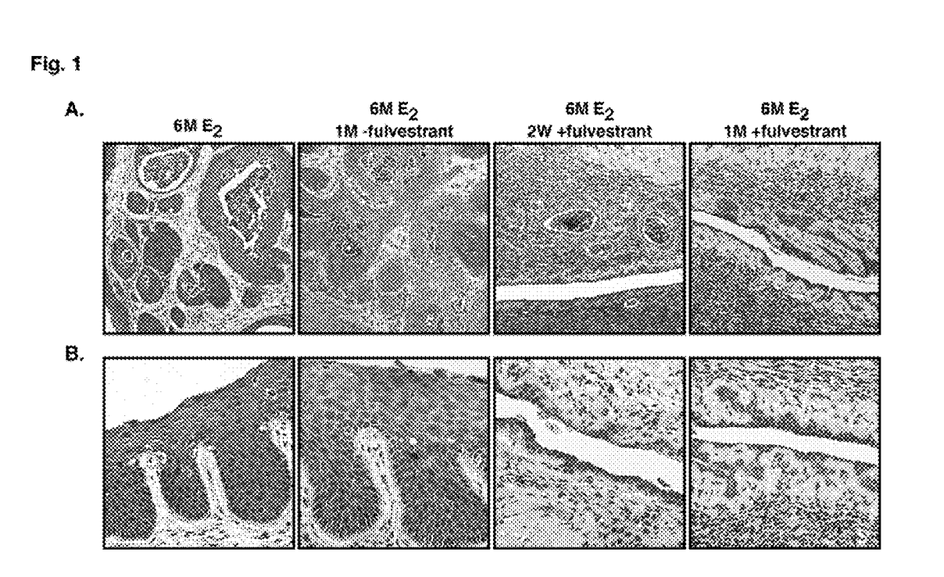
FIG. 1. One-month fulvestrant treatment results in regression of cervical cancer as well as dysplasia.

Potential implication of cancers persisting after fulvestrant treatment. It was immediately noted that epithelia of lower reproductive tracts from fulvestrant-treated mice with thin with only 2-3 layers of cells, indicating that ERα function is crucial for thickening of cervical/vaginal epithelium (FIG. 1). This result is in agreement with the observation that lower reproductive tract epithelium is hypoplastic in ERα-deficient tissue recombinant (Buchanan et al., 1998) and mice (Chung et al., 2008). Unclear is the nature of glassiness in cervical epithelium of fulvestrant-treated mice and glassiness increases as treated with fulvestrant for longer periods of time (FIG. 1). Glassy epithelia were less prominent in the vagina compared to the cervix (data not shown). It was particularly interesting to note that epithelia near the cancers remaining after 1M-fulvestrant treatment were as thick as those in mice not treated with fulvestrant (FIG. 2), indicating that fulvestrant is not so effective in those specific areas as in other regions in these mice. One possibility is that in these cases, the cancers and/or the associated stroma are producing their own estrogen, which leads to locally elevated estrogen concentrations that are sufficient to suppress fulvestrant's antagonistic function locally. If this prediction is correct, then aromatase inhibitors in conjunction with fulvestrant may potentially be more effective in controlling such lower reproductive tract cancers.

Figure 2:
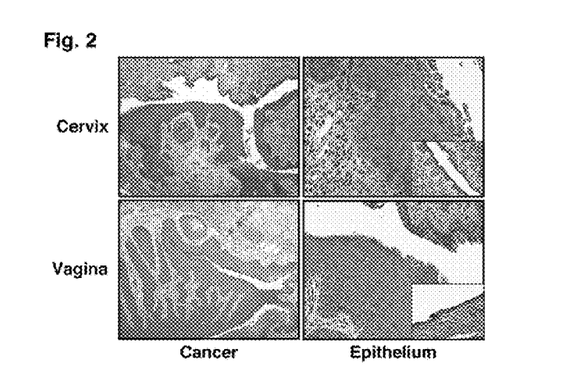

Fulvestrant causes regression of dysplastic lesions. In the histopathological analyses of lower reproductive tracts, we also observed the absence of any grade of dysplastic lesions (CIN and VIN) in mice treated with estrogen for 6 months and then administered fulvestrant for 1 month, whereas dysplasias were found in the entire lower reproductive tracts of mice treated with estrogen but not with fulvestrant (FIG. 1B). Dysplastic lesions were also absent in mice treated with estrogen for 6 months and then with fulvestrant for two weeks even though these animals still had cancers in the lower reproductive tracts (FIG. 1). Furthermore, only focal dysplastic lesions were observed in the epithelia of mice still bearing cancers after fulvestrant treatment for a month (FIG. 2). These results indicate that fulvestrant is effective in treating not only cervical/vaginal cancers but also dysplastic lesions in the female lower reproductive tracts of mice.

Potential use of anti-estrogen therapy for lower reproductive tract disease in women. Results of our current study strongly suggest that anti-estrogen therapy could be effective for treating and/or preventing lower reproductive tract disease including cancers in women. There is no indication that fulvestrant, the anti-estrogen used in this study, has estrogenic effect in women. However, this complete anti-estrogenic property may not be necessarily beneficial for long-term therapy because absence of estrogen function may cause other clinical symptoms seen in postmenopausal women. In this regard, raloxifene might be a better option because it shows protective effect on bone and cardiovascular system, whereas it has anti-estrogenic activity in breast and uterine tissues (Shelly et al., 2008). Therefore, we carried out additional studies and found that raloxifene also can eliminate pre-existing cervical diseases including cervical cancer (See Example 2, below). If estrogen is necessary for lower reproductive tract disease in women, aromatase inhibitors are anticipated to be as effective as anti-estrogens because they will also inhibit ER by inhibiting synthesis of its ligand estrogen. This is potentially relevant to our observation that some mice that were treated with estrogen for 6 months and then fulvestrant for another month still had cancers with adjacent epithelium with normal thickness (FIG. 2). In this context, it is known that some human cervical cancers synthesize estrogen by over-expressing aromatase, a key enzyme in estrogen biosynthesis (Nair et al., 2005).

TABLE 1

State of Lower Reproductive Tract Disease[1].

| Treatment[2] | Total number of mice | No dysplasia | Dysplasia | | | Cervical (vaginal) cancer |
| --- | --- | --- | --- | --- | --- | --- |
| | | | CIN1 (VIN1) | CIN2 (VIN2) | CIN3 (VIN3) | |
| 6M $E_2$ | 6 | 0 | 0 (0) | 0 (0) | 0 (2) | 6 (3) |
| 6M $E_2$ + 1M without fulvestrant | 14 | 0 | 0 (0) | 0 (3) | 3 (6) | 11 (5) |
| 6M $E_2$ + 1M with fulvestrant | 13 | 11 | 0 (0) | 0 (0) | 0 (0) | 1 (1) |

[1]Mice were scored histopathologically for the worst state of disease present in the cervix or, in parentheses, the vagina. The numbers of mice with the indicated state of disease are indicated in each column.
[2]Female reproductive tracts were harvested immediately after 6-month treatment of estrogen (first row). Mice were treated with estrogen for 6 months and then further kept for another month without (second row) or with (third row) fulvestrant treatment.
CIN, cervical intraepithelial neoplasia;
VIN, vaginal intraepithelial neoplasia.
Note:
for Wilcoxon rank sum test (see text), CIN (VIN) lesions were given the following arbitrary score; no dysplasia = 1; CIN1 (VIN1) = 2; CIN2 (VIN2) = 3; CIN3 (VIN3) = 4; cancer = 5.

TABLE 2

Comparison of cancers in estrogen-treated K14E6/K14E7 mice with a different scheme of further treatment with fulvestrant.

| Treatment[1] | Cancer incidence (%) | Average size of the largest tumor (mm$^2$) | Tumor multiplicity Cervix | Vagina |
|---|---|---|---|---|
| 6M E$_2$ | 100[2] | 0.44 ± 0.57[2] | 3.3 ± 1.1[2,3] | 0.5 ± 0.5 |
| 6M E$_2$ + 1M without fulvestrant | 93[2] | 0.28 ± 0.29[2] | 2.3 ± 1.4[2,3] | 0.4 ± 0.6 |
| 6M E$_2$ + 1M with fulvestrant | 15 | 0.02 ± 0.05 | 0.2 ± 0.5 | 0.1 ± 0.3 |

[1]Treatment groups are identical to those described in Table 1.
[2]Compared with 6M E2 + 1M with fulvestrant, p < 0.008, two-sided Fisher's exact test (cancer incidence) or Wilcoxon rank sum test (tumor sizes and multiplicities).
[3]Compared with vaginal cancer multiplicity, p < 0.008, two-sided Wilcoxon rank sum test.

Example 2

Raloxifene Promotes Regression of Cervical/Vaginal Disease Including Cancers EVISTA® tablets were purchased from Eli Lilly and Company, which are human formulation of raloxifene (60 mg/tablet). Tablets were resuspended in phosphate buffered saline at a final concentration of 10 mg/ml. K14E6/K14E7 double transgenic mice were treated with E2 for 6 months and subsequently with raloxifene for a month by intraperitoneally injecting them with 0.15 ml of raloxifene suspension (equivalent to 1.5 mg) 5 days a week. A preferred human dosage is 60 mg daily. As shown in Table 3, raloxifene treatment induced complete regression of cervical and vaginal disease including cancers.

TABLE 3

Comparison of cervical/vaginal disease in E2-treated K14E6/K14E7 mice with or without raloxifene (Ral) treatment.

| Treatment group (group size) | # mice with no dysplasia or cancer | | # mice w/dysplasia only | | | # mice w/cancer and dysplasia (%) | |
|---|---|---|---|---|---|---|---|
| | Cervix | Vagina | CIN1 (VIN1) | CIN2 (VIN2) | CIN3 (VIN3) | Cervix | Vagina |
| 6M E2 + 1M without Ral | 0 | 0 | 0 (0) | 0 (3) | 3 (6) | 11 (79) | 5 (36) |
| 6M E2 + 1M with Ral | 7 | 6 | 0 (0) | 0 (0) | 0 (1) | 0 (0) | 0 (0) |

CIN, cervical intraepithelial neoplasia;
VIN, vaginal intraepithelial neoplasia.
Note:
for Wilcoxon rank sum test, arbitrary scores were given to each lesion as following; no dysplasia = 1; CIN1 (VIN1) = 2; CIN2 (VIN2) = 3; CIN3 (VIN3) = 4; cancer = 5.
Two-sided statistical analyses on two groups (6M E2 + 1M without Ral vs. 6M E2 + 1M with Ral), cervical cancer incidence p = 0.001 (Fisher's exact test); cervical disease p = 0.00005 (Wilcoxon rank sum test); vaginal cancer incidence p = 0.12 (Fisher's exact test); vaginal disease p = 0.0009 (Wilcoxon rank sum test).

Example 3

Fulvestrant Treatment Prevents the Development of Cervical/Vaginal Cancers

CIN and VIN are thought to be the precursor lesions to cervical and vaginal cancers, respectively. Because these lesions largely disappeared in the 6M E2+1M with fulvestrant and 6M E2+1M with Ral groups, we performed an additional experiment to determine whether fulvestrant can prevent the onset of cervical/vaginal cancers.

To address this issue we began treating mice with fulvestrant after only three months of E2 treatment, a time period at which CIN/VIN are present but no cancers have yet developed (Table 4, 3M E2 group). Mice treated with fulvestrant for one month at the three-month time point (6M E2+preventative fulvestrant group) showed neither CIN nor cervical cancer at the six-month endpoint. These phenotypes are significantly different from those of the 6M E2 group that had not received fulvestrant (p=0.002, cancer incidence; p=0.0009, cervical disease). Thus, fulvestrant not only promotes regression of cervical cancer but also prevents the development of this malignancy in mice. The 6M E2+preventative fulvestrant group also displayed a significantly lower degree of vaginal disease compared to the 6M E2 group (p=0.002). These data indicate that treatment with an antiestrogen can prevent progression of precancerous lesions. This, together with our data showing a therapeutic effect on treating existing cancer also lead to the prediction that antiestrogens could be useful in preventing recurrence of cervical/vaginal cancers in women.

TABLE 4

Comparison of cervical/vaginal disease in E2-treated K14E6/K14E7 mice with or without fulvestrant treatment.

| Treatment group (group size) | # mice with no dysplasia or cancer | | # mice w/dysplasia only | | | # mice w/cancer and dysplasia (%) | |
|---|---|---|---|---|---|---|---|
| | Cervix | Vagina | CIN1 (VIN1) | CIN2 (VIN2) | CIN3 (VIN3) | Cervix | Vagina |
| 3M E2 (n = 6) | 0 | 2 | 1 (2) | 3 (2) | 2 (0) | 0 (0) | 0 (0) |
| 6M E2 + preventive fulvestrant | 6 | 6 | 0 (0) | 0 (0) | 0 (0) | 0 (0) | 0 (0) |
| 6M E2 (n = 6) | 0 | 0 | 0 (0) | 0 (1) | 0 (2) | 6 (100) | 3 (50) |

Example 4

Estrogen Facilitates Tumor Formation by a Human Cervical Cancer Cell Line in Nude Mice and Fulvestrant Inhibits Tumor Growth Methods:

Cell lines CVX1 (Bellone et al., 2003) and CIN612E (Bedell et al., 1991) cells were maintained in a mixture of DMEM and F12 (3:1) supplemented with 5% fetal bovine serum (FBS), 0.4 µg/ml hydrocortisone, 5 µg/ml insulin, 0.1 nM cholera toxin, 24.2 µg/ml adenine, 10 ng/ml epidermal growth factor, 10 Unit/ml penicillin and 10 µg/ml streptomycin. The other cells (see FIG. 3) were grown in DMEM containing 10% FBS and penicillin/streptomycin (All cell culture media are available from GIBCO® Invitrogen Corp., Carlsbad, Calif.).

Immunoblot Cells were lysed in RIPA buffer (50 mM Tris-CI, pH 8.0, 150 mM NaCl, 1% NP-40 detergent, 0.5% sodium deoxycholate, 0.1% SDS) supplemented with proteinase inhibitors and phosphatase inhibitors. Protein concentration was determined by Bradford method and equal amount of lysates were resolved on 10% SDS-polyacrylamide gel. Proteins were transferred to a PVDF membrane and blocked with 5% nonfat milk in TBS-T (50 mM Tris-CI, pH 7.5, 200 mM NaCl, 0.2% Tween-20). The membrane was incubated with either anti-ERα (Santa Cruz Biotechnology) or anti-actin antibody (Santa Cruz Biotechnology) diluted in TBS-T containing 0.5% nonfat milk (1:1000 dilution for anti-ERα; 1:2500 for anti-actin), and then with horseradish peroxidase-conjugated goat anti-rabbit IgG (Jackson Immunoresearch Laboratories, Inc., West Grove, Pa.) diluted (1:5000) in TBS-T containing 0.5% nonfat milk. After extensive washes, membranes were developed by enhanced chemilluminescent methods (Pierce Protein Research Products, Thermo Fisher Scientific, Rockford, Ill.) as described in the manufacturer's instructions.

Mice treatment Six-week old female nude mice were purchased from Harlan™. Groups of mice were implanted subcutaneously with estrogen pellets that slowly release 0.05 mg of estrogen over 60 days. This regimen results in estrogen concentration in serum just enough to keep animals in persistent estrus. One week after estrogen treatment, $10^7$ cells (CVX1) or $10^6$ cells (CaSki and SiHa) were subcutaneously injected at the flank. A subset of mice was also subcutaneously injected with 7.5 mg of fulvestrant twice a week once tumors formed. Tumor size was measured regularly using a slide caliper.

Figure 3:
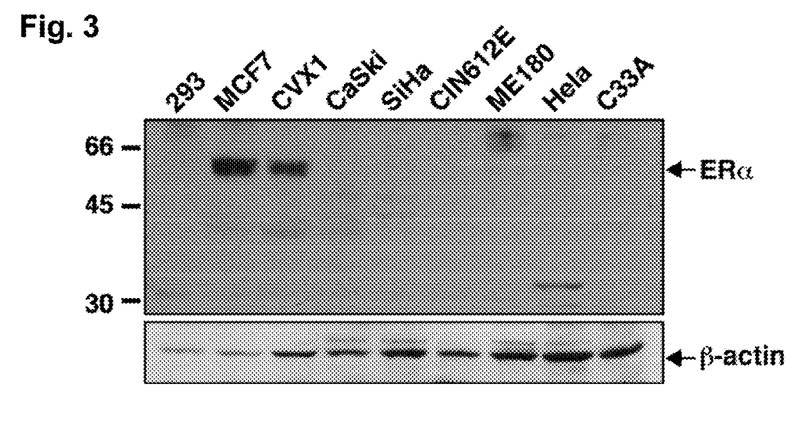
FIG. 3. Screening for ERα-positive human cervical cancer cell lines. Various cervical cell lines were examined for ERα expression by immunoblotting with an anti-ERα antibody (H184 from Santa Cruz Biotechnology, Inc., Santa Cruz, Calif.). The cell lines screened include: 293, an ERα⁻ epithelial cell line (human; negative control); MCF7, an ERα⁺ breast cancer cell line (positive control); CasKi; SiHa; ME180; Hela (purchased from ATCC; CVX1 (Bellone et al., 2003), an HPV⁺ cervical cancer cell line; C33A, an HPV⁻ cervical cancer cell line; and CIN612E (Bedell et al., 1991), an HPV⁺ cervical dysplasia cell line. Actin was used as a loading control.
Figure 4:
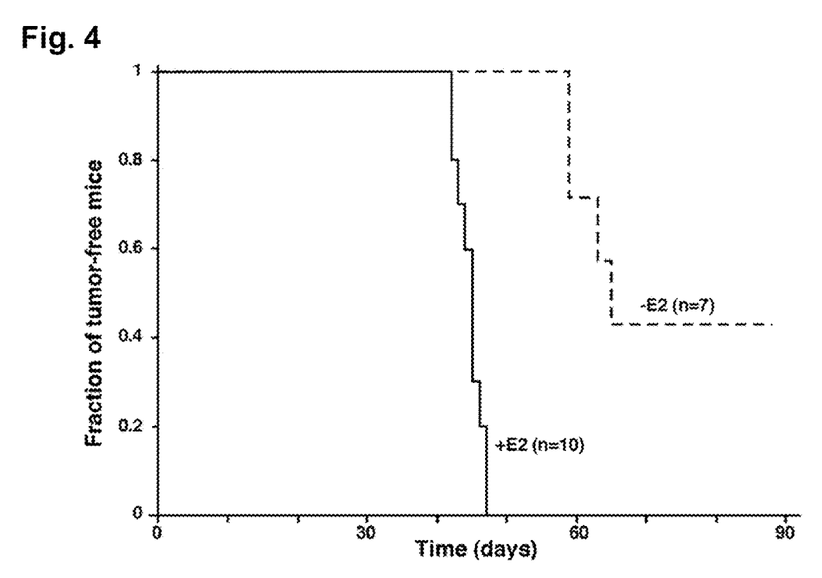
FIG. 4. Formation of tumors in nude mice subcutaneously injected with CVX1 human cervical cancer cells. CVX1 cells were subcutaneously injected into nude mice that were either untreated (−E2) or estrogen-treated (+E2). Tumor formation was monitored, and tumor-free state was plotted with a Kaplan Meier curve.

Results Although it is clear from prior studies in HPV16 transgenic mice that the estrogen-ERα pathway is crucial for cervical cancer in mice (Chung et al., 2008), and ER antagonists are effective in controlling this malignancy (Chung and Lambert, 2009), it is not known if the same is true for cervical cancer in women. To address this we pursued studies making use of cell lines derived from human cervical cancers. We first screened multiple human cervical cancer cell lines for ERα expression by immunoblot analysis (FIG. 3). ERα expression was undetectable in widely used cervical cancer cell lines, CaSki, SiHa, HeLa, and C33A that have been grown in laboratory tissue culture for decades. However, we found that a relatively newly established, low passage cervical cancer cell line, CVX1, retains expression of ERα. This is consistent with ERα-positive status of human cervical cancers in vivo (Chung et al., 2008). Importantly, exogenous estrogen facilitated tumor formation by this cell line in athymic nude mice (FIG. 4) (p=0.001, Log rank test). Whereas 4 out of 7 mice that were not treated with exogenous estrogen developed tumors, all estrogen-treated mice developed tumors (p=0.05, two-sided Fisher's exact test). In addition, tumor latency in untreated mice was significantly higher than in estrogen-treated mice (62 days vs. 46 days; p=0.003, two-sided Wilcoxon rank sum test). In contrast, exogenous estrogen had no effect on tumorigenic properties of ERα-negative cervical cancer cell lines SiHa and CaSki. Both cell lines formed tumors in all animals (n=4 each group) at 15 days after injection regardless of estrogen treatment (data not shown).

Figure 5:
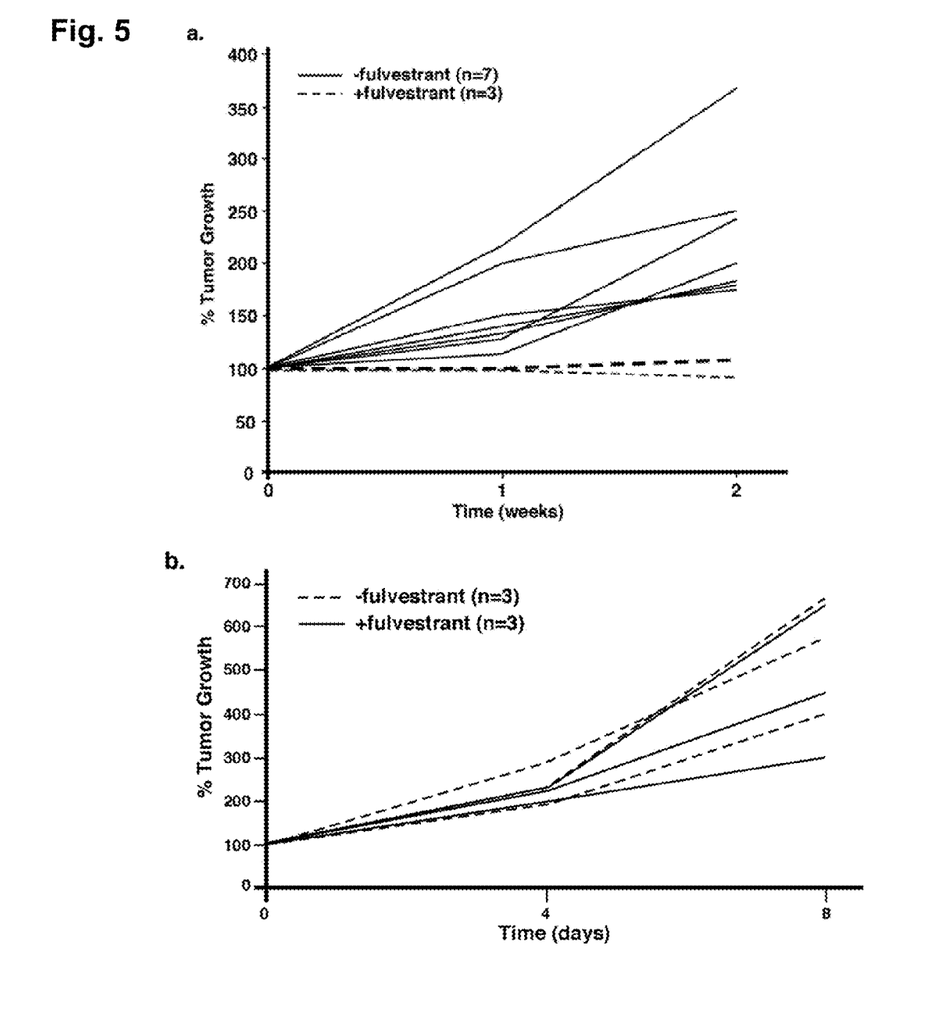

To assess whether ERα-antagonists can inhibit the tumorigenic growth of human cervical cancer derived cell lines, we took mice that had been injected subcutaneously with human cervical cancer cell lines, waited for tumors to develop, and then treated them with fulvestrant. Fulvestrant blocked tumor growth of the ERα-positive CVX1 cancer cell line but did not block tumor growth of the ERα-negative CaSki cell line (FIG. 5). Specifically, within the two-week time treatment period, CVX1 tumors grew 2.5 fold without fulvestrant-treatment but did not grow at all with the treatment (p=0.02, two-sided Wilcoxon rank sum test). In contrast, CaSki tumors grew 4.7 or 5.1 fold with or without fulvestrant treatment, respectively (p=0.51). These results provide further proof, consistent with that obtained with our HPV transgenic mouse model, that human cervical cancers that express ERα depend on estrogen for their growth and respond favorably to treatment with an ERα-antagonist.

REFERENCES

Althuis, M. D., Moghissi, K. S., Westhoff, C. L., Scoccia, B., Lamb, E. J., Lubin, J. H., and Brinton, L. A. (2005a). Uterine cancer after use of clomiphene citrate to induce ovulation. Am J Epidemiol 161, 607-615.

Althuis, M. D., Scoccia, B., Lamb, E. J., Moghissi, K. S., Westhoff, C. L., Mabie, J. E., and Brinton, L. A. (2005b). Melanoma, thyroid, cervical, and colon cancer risk after use of fertility drugs. Am J Obstet Gynecol 193, 668-674.

Ariazi, E. A., Lewis-Wambi, J. S., Gill, S. D., Pyle, J. R., Ariazi, J. L., Kim, H. R., Sharma, C. G., Cordera, F., Shupp, H. A., Li, T., and Jordan, V. C. (2006). Emerging principles for the development of resistance to antihormonal therapy: implications for the clinical utility of fulvestrant. J Steroid Biochem Mol Biol 102, 128-138

Bedell M., J. Hudson, T. Golub, M. Turyk, M. Hosken, G. Wilbanks and L. Laimins. 1991. Amplification of human papillomavirus genomes in vitro is dependent on epithelial differentiation. *J. Virol.* 65: 2254-2260.

Bellone S, Palmieri M, Gokden M, Joshua J, Roman J J, Pecorelli S, Cannon M J, and Santin A D. 2003. Selection of HER-2/neu-positive tumor cells in early stage cervical cancer: implications for Herceptin-mediated therapy. Gynecol Oncol. 91: 231-240.

Bigler, L. R., Tate Thigpen, J., Blessing, J. A., Fiorica, J., and Monk, B. J. (2004). Evaluation of tamoxifen in persistent or recurrent nonsquamous cell carcinoma of the cervix: a Gynecologic Oncology Group study. Int J Gynecol Cancer 14, 871-874.

Brake, T., Connor, J. P., Petereit, D. G., and Lambert, P. F. (2003). Comparative analysis of cervical cancer in women and in a human papillomavirus-transgenic mouse model: identification of minichromosome maintenance protein 7 as an informative biomarker for human cervical cancer. Cancer Res 63, 8173-8180.

Brake, T., and Lambert, P. F. (2005). Estrogen contributes to the onset, persistence, and malignant progression of cervical cancer in a human papillomavirus-transgenic mouse model. Proc Natl Acad Sci USA 102, 2490-2495.

Buchanan, D. L., Kurita, T., Taylor, J. A., Lubahn, D. B., Cunha, G. R., and Cooke, P. S. (1998). Role of stromal and epithelial estrogen receptors in vaginal epithelial proliferation, stratification, and cornification. Endocrinology 139, 4345-4352.

Burd, E. M. (2003). Human papillomavirus and cervical cancer. Clin Microbiol Rev 16, 1-17.

Cavalieri, E., Chakravarti, D., Guttenplan, J., Hart, E., Ingle, J., Jankowiak, R., Muti, P., Rogan, E., Russo, J., Santen, R., and Sutter, T. (2006). Catechol estrogen quinones as initiators of breast and other human cancers: implications for biomarkers of susceptibility and cancer prevention. Biochim Biophys Acta 1766, 63-78.

Chung S H, Wiedmeyer K, Shai A, Korach K S, and Lambert P F. 2008. Requirement for estrogen receptor alpha in a mouse model for human papillomavirus-associated cervical cancer. Cancer Res. 68: 9928-9934.

Chung S H and Lambert P F. 2009. Prevention and treatment of cervical cancer in mice using estrogen receptor antagonists. *Proc. Natl. Acad. Sci. U.S.A.* 106:19467-19472.

Couse, J. F., and Korach, K. S. (1999). Estrogen receptor null mice: what have we learned and where will they lead us? Endocr Rev 20, 358-417.

Elson, D. A., Riley, R. R., Lacey, A., Thordarson, G., Talamantes, F. J., and Arbeit, J. M. (2000). Sensitivity of the cervical transformation zone to estrogen-induced squamous carcinogenesis. Cancer Res 60, 1267-1275.

Friedrich, M., Mink, D., Villena-Heinsen, C., Woll-Hermann, A., and Schmidt, W. (1998). Tamoxifen and proliferation of vaginal and cervical epithelium in postmenopausal women with breast cancer. Eur J Obstet Gynecol Reprod Biol 80, 221-225.

FUTURE II Group (2007). Quadrivalent vaccine against human papillomavirus to prevent high-grade cervical lesions. N Engl J Med 356, 1915-1927.

Heldring, N., Pike, A., Andersson, S., Matthews, J., Cheng, G., Hartman, J., Tujague, M., Strom, A., Treuter, E., Warner, M., and Gustafsson, J. A. (2007). Estrogen receptors: how do they signal and what are their targets. Physiol Rev 87, 905-931.

Herber, R., Liem, A., Pitot, H., and Lambert, P. F. (1996). Squamous epithelial hyperplasia and carcinoma in mice transgenic for the human papillomavirus type 16 E7 oncogene. J Virol 70, 1873-1881.

Herynk, M. H., and Fuqua, S. A. (2004). Estrogen receptor mutations in human disease. Endocr Rev 25, 869-898.

Hunter, M. I., Monk, B. J., and Tewari, K. S. (2008a). Cervical neoplasia in pregnancy. Part 1: screening and management of preinvasive disease. Am J Obstet Gynecol 199, 3-9.

Hunter, M. I., Tewari, K., and Monk, B. J. (2008b). Cervical neoplasia in pregnancy. Part 2: current treatment of invasive disease. Am J Obstet Gynecol 199, 10-18.

Lerner-Geva, L., Keinan-Boker, L., Blumstein, T., Boyko, V., Olmar, L., Mashiach, S., Rabinovici, J., Potashnik, G., Lunenfeld, E., Schenker, J. G., et al. (2006). Infertility, ovulation induction treatments and the incidence of breast cancer—a historical prospective cohort of Israeli women. Breast Cancer Res Treat 100, 201-212.

Moreno, V., Bosch, F. X., Munoz, N., Meijer, C. J., Shah, K. V., Walboomers, J. M., Herrero, R., and Franceschi, S. (2002). Effect of oral contraceptives on risk of cervical cancer in women with human papillomavirus infection: the IARC multicentric case-control study. Lancet 359, 1085-1092.

Munoz, N., Franceschi, S., Bosetti, C., Moreno, V., Herrero, R., Smith, J. S., Shah, K. V., Meijer, C. J., and Bosch, F. X. (2002). Role of parity and human papillomavirus in cervical cancer: the IARC multicentric case-control study. Lancet 359, 1093-1101.

Nair, H. B., Luthra, R., Kirma, N., Liu, Y. G., Flowers, L., Evans, D., and Tekmal, R. R. (2005). Induction of aromatase expression in cervical carcinomas: effects of endogenous estrogen on cervical cancer cell proliferation. Cancer Res 65, 11164-11173.

Palmieri, C., Cheng, G. J., Saji, S., Zelada-Hedman, M., Warri, A., Weihua, Z., Van Noorden, S., Wahlstrom, T., Coombes, R. C., Warner, M., and Gustafsson, J. A. (2002). Estrogen receptor beta in breast cancer. Endocr Relat Cancer 9, 1-13.

Persson, I., Yuen, J., Bergkvist, L., and Schairer, C. (1996). Cancer incidence and mortality in women receiving estrogen and estrogen-progestin replacement therapy—long-term follow-up of a Swedish cohort. Int J Cancer 67, 327-332.

Riley, R. R., Duensing, S., Brake, T., Munger, K., Lambert, P. F., and Arbeit, J. M. (2003). Dissection of human papillomavirus E6 and E7 function in transgenic mouse models of cervical carcinogenesis. Cancer Res 63, 4862-4871.

Rossing, M. A., Daling, J. R., Weiss, N. S., Moore, D. E., and Self, S. G. (1996). In situ and invasive cervical carcinoma in a cohort of infertile women. Fertil Steril 65, 19-22.

Sankaranarayanan, R., and Ferlay, J. (2006). Worldwide burden of gynaecological cancer: the size of the problem. Best Pract Res Clin Obstet Gynaecol 20, 207-225.

Schiffman, M., Castle, P. E., Jeronimo, J., Rodriguez, A. C., and Wacholder, S. (2007). Human papillomavirus and cervical cancer. Lancet 370, 890-907.

Shai, A., Brake, T., Somoza, C., and Lambert, P. F. (2007). The human papillomavirus E6 oncogene dysregulates the cell cycle and contributes to cervical carcinogenesis through two independent activities. Cancer Res 67, 1626-1635.

Shelly, W., Draper, M. W., Krishnan, V., Wong, M., and Jaffe, R. B. (2008). Selective estrogen receptor modulators: an update on recent clinical findings. Obstet Gynecol Sury 63, 163-181.

Song, S., Pitot, H. C., and Lambert, P. F. (1999). The human papillomavirus type 16 E6 gene alone is sufficient to induce carcinomas in transgenic animals. J Virol 73, 5887-5893.

Villa, L. L. (2007). Overview of the clinical development and results of a quadrivalent HPV (types 6, 11, 16, 18) vaccine. Int J Infect Dis 11, 17-25.

Woodman, C. B., Collins, S. I., and Young, L. S. (2007). The natural history of cervical HPV infection: unresolved issues. Nat Rev Cancer 7, 11-22.

zur Hausen, H. (2002). Papillomaviruses and cancer: from basic studies to clinical application. Nat Rev Cancer 2, 342-350.

We claim:

1. A method for preventing cervical or vaginal cancer in patients with dysplasia comprising the steps of
    (a) identifying a dysplasia (CIN/VIN) patient,
    (b) administering an effective amount of an estrogen antagonist therapy to the patient, wherein the amount is effective to reduce dysplasia and prevent cervical cancer; and
    (c) measuring a reduction of dysplasia and absence or slowing of progression to cervical/vaginal cancer.

2. The method of claim 1 wherein the estrogen antagonist is selected from fulvestrant and raloxifene.

3. The method of claim 1 wherein the estrogen antagonist is a selective estrogen receptor modulator with antagonistic effects in the cervix/vagina.

* * * * *

UNITED STATES PATENT AND TRADEMARK OFFICE
CERTIFICATE OF CORRECTION

| | |
|---|---|
| PATENT NO. | : 8,158,614 B2 |
| APPLICATION NO. | : 12/693850 |
| DATED | : April 17, 2012 |
| INVENTOR(S) | : Paul F. Lambert et al. |

It is certified that error appears in the above-identified patent and that said Letters Patent is hereby corrected as shown below:

Delete the title page and substitute therefore with the attached title page showing the corrected number of claims in patent.

In the Claims

Column 20, Line 15 - INSERT

--4. The method of claim 1 further comprising the step of administering at least one of an aromatase inhibitor and a chemotherapeutic agent.--

Signed and Sealed this
Fifteenth Day of July, 2014

Michelle K. Lee
*Deputy Director of the United States Patent and Trademark Office*

(12) United States Patent
Lambert et al.

(10) Patent No.: US 8,158,614 B2
(45) Date of Patent: Apr. 17, 2012

(54) THERAPEUTIC TREATMENT OF CANCER AND DYSPLASIA OF THE CERVIX OR VAGINA USING ESTROGEN ANTAGONISTS

(75) Inventors: Paul F. Lambert, Madison, WI (US); SangHyuk Chung, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 26 days.

(21) Appl. No.: 12/693,850

(22) Filed: Jan. 26, 2010

(65) Prior Publication Data

US 2010/0203164 A1    Aug. 12, 2010

Related U.S. Application Data

(60) Provisional application No. 61/147,667, filed on Jan. 27, 2009, provisional application No. 61/148,445, filed on Jan. 30, 2009, provisional application No. 61/261,615, filed on Nov. 16, 2009.

(51) Int. Cl.
| | |
|---|---|
| A61K 31/56 | (2006.01) |
| A61K 31/445 | (2006.01) |
| A01N 43/40 | (2006.01) |
| A01N 43/02 | (2006.01) |

(52) U.S. Cl. ............ 514/182; 514/324; 514/449
(58) Field of Classification Search ............. None
See application file for complete search history.

(56) References Cited

U.S. PATENT DOCUMENTS 6,433,000 B1   8/2002   Li et al.

FOREIGN PATENT DOCUMENTS

| WO | 2005/108338 A1 | 11/2005 |
| WO | 2009/034136 A2 | 3/2009 |

OTHER PUBLICATIONS

Althuis, M. D., Moghissi, K. S., Westhoff, C. L., Scoccia, B., Lamb, E. J., Lubin, J. H., and Brinton, L. A. (2005a). Uterine cancer after use of clomiphene citrate to induce ovulation. Am J Epidemiol 161, 607-615.
2. Althuis, M. D., Scoccia, B., Lamb, E. J., Moghissi, K. S., Westhoff, C. L., Mabie, J. E., and Brinton, L. A. (2005b). Melanoma, thyroid, cervical, and colon cancer risk after use of fertility drugs. Am J Obstet Gynecol 193, 668-674.
Ariazi, E. A., Lewis-Wambi, J. S., Gill, S. D., Pyle, J. R., Ariazi, J. L., Kim, H. R., Sharma, C. G., Cordera, F., Shupp, H. A., Li, T., and Jordan, V. C. (2006). Emerging principles for the development of resistance to antihormonal therapy: implications for the clinical utility of fulvestrant. J Steroid Biochem Mol Biol 102, 128-138.
Brake, T., Connor, J. P., Petereit, D. G., and Lambert, P. F. (2003). Comparative analysis of cervical cancer in women and in a human papillomavirus-transgenic mouse model: identification of minichromosome maintenance protein 7 as an informative biomarker for human cervical cancer. Cancer Res 63, 8173-8180.
Brake T., and Lambert, P. F. (2005). Estrogen contributes to the onset, persistence, and malignant progression of cervical cancer in a human papillomavirus-transgenic mouse model. Proc Natl Acad Sci U S A 102, 2490-2495.
Buchanan D. L., Kurita, T., Taylor, J. A., Lubahn, D. B., Cunha, G. R., and Cooke, P. S. (1998). Role of stromal and epithelial estrogen receptors in vaginal epithelial proliferation, stratification, and cornification. Endocrinology 139, 4345-4352.
Cavalieri E., Chakravarti, D., Guttenplan, J., Hart, E., Ingle, J., Jankowiak, R., Muti, P., Rogan, E., Russo, J., Santen, R., and Sutter, T. (2006). Catechol estrogen quinones as initiators of breast and other human cancers: implications for biomarkers of susceptibility and cancer prevention. Biochim Biophys Acta 1766, 63-78.
Chung SH, Wiedmeyer K, Shai A, Korach KS, and Lambert PF, 2008. Requirement for estrogen receptor alpha in a mouse model for human papillomavirus-associated cervical cancer. Cancer Res. 68: 9928-9934.
Chung SH and Lambert PF. 2009. Prevention and treatment of cervical cancer in mice using estrogen receptor antagonists. Proc. Natl. Acad. Sci. U. S. A. 106: 19467-19472.
Elson D. A., Riley, R. R., Lacey, A., Thordarson, G., Talamantes, F. J., and Arbeit, J. M. (2000). Sensitivity of the cervical transformation zone to estrogen-induced squamous carcinogenesis. Cancer Res 60, 1267-1275.
Friedrich M., Mink, D., Villena-Heinsen, C., Woll-Hermann, A., and Schmidt, W. (1998). Tamoxifen and proliferation of vaginal and cervical epithelium in postmenopausal women with breast cancer. Eur J Obstet Gynecol Reprod Biol 80, 221-225.
Heldring, N., Pike, A., Andersson, S., Matthews, J., Cheng, G., Hartman, J., Tujague, M., Strom, A., Treuter, E., Warner, M., and Gustafsson, J. A. (2007). Estrogen receptors: how do they signal and what are their targets. Physiol Rev 87, 905-931.
Moreno, V., Bosch, F. X., Munoz, N., Meijer, C. J., Shah, K. V., Walboomers, J. M., Herrero, R., and Franceschi, S. (2002). Effect of oral contraceptives on risk of cervical cancer in women with human papillomavirus infection: the IARC multicentric case-control study. Lancet 359, 1085-1092.
Munoz, N., Franceschi, S., Bosetti, C., Moreno, V., Herrero, R., Smith, J. S., Shah, K. V., Meijer, C. J., and Bosch, F. X. (2002). Role of parity and human papillomavirus in cervical cancer: the IARC multicentric case-control study. Lancet 359, 1093-1101. Nair, H. B., Luthra, R., Kirma, N., Liu, Y. G., Flowers, L., Evans, D., and Tekmal, R. R. (2005). Induction of aromatase expression in cervical carcinomas: effects of endogenous estrogen on cervical cancer cell proliferation. Cancer Res 65, 11164-11173.
Palmieri C., Cheng, G. J., Saji, S., Zelada-Hedman, M., Warri, A., Weihua, Z., Van Noorden, S., Wahlstrom, T., Coombes, R. C., Warner, M., and Gustafsson, J. A. (2003). Estrogen receptor beta in breast cancer. Endocr Relat Cancer 9, 1-13.
Riley R R., Duensing, S., Brake, T., Munger, K., Lambert, P. F., and Arbeit, J. M. (2003). Dissection of human papillomavirus E6 and E7 function in transgenic mouse models of cervical carcinogenesis. Cancer Res 63, 4862-4871.
Rossing, M. A., Daling, J. R., Weiss, N. S., Moore, D. E., and Self, S. G. (1996). In situ and invasive cervical carcinoma in a cohort of infertile women. Fertil Steril 65, 19-22.

(Continued)

*Primary Examiner* — Brandon Fetterolf
*Assistant Examiner* — Anna Pagonakis
(74) *Attorney, Agent, or Firm* — Quarles & Brady LLP (57) ABSTRACT

A method for treatment of cervical or vaginal cancer and their associated dysplasia, including the steps of identifying a human cervical or vaginal cancer and/or dysplasia patient, administering an effective amount of an estrogen antagonist therapy to the patient, wherein the amount is effective to reduce cancer and dysplasia symptoms, and observing a reduction of cancer and dysplasia symptoms in the patient.

4 Claims, 3 Drawing Sheets